(12) United States Patent
Issa et al.

(10) Patent No.: US 11,523,765 B2
(45) Date of Patent: Dec. 13, 2022

(54) NEUROPHYSIOLOGICAL BIOMARKERS FOR NEURODEGENERATIVE DISORDERS

(71) Applicant: The University of Chicago, Chicago, IL (US)

(72) Inventors: Naoum P. Issa, Chicago, IL (US); Kourosh Rezania, Chicago, IL (US)

(73) Assignee: The University of Chicago, Chicago, IL (US)

( * ) Notice: Subject to any disclaimer, the term of this patent is extended or adjusted under 35 U.S.C. 154(b) by 23 days.

(21) Appl. No.: 16/561,981

(22) Filed: Sep. 5, 2019

(65) Prior Publication Data
US 2020/0069204 A1 Mar. 5, 2020

Related U.S. Application Data

(60) Provisional application No. 62/727,362, filed on Sep. 5, 2018.

(51) Int. Cl.
*A61B 5/00* (2006.01)
*A61B 5/316* (2021.01)
*A61B 5/389* (2021.01)

(52) U.S. Cl.
CPC .............. *A61B 5/316* (2021.01); *A61B 5/389* (2021.01); *A61B 5/4082* (2013.01); *A61B 5/4088* (2013.01); *A61B 5/4842* (2013.01); *A61B 5/6824* (2013.01)

(58) Field of Classification Search
CPC ....... A61B 5/316; A61B 5/389; A61B 5/4842; A61B 5/4088; A61B 5/6824; A61B 5/4082

USPC .................................................. 600/301, 546
See application file for complete search history.

(56) References Cited

U.S. PATENT DOCUMENTS

| | | | |
|---|---|---|---|
| 5,505,208 A * | 4/1996 | Toomim ................. | A61B 5/389 600/546 |
| 8,167,799 B2 * | 5/2012 | Ronchi ................ | A61B 5/1126 600/301 |
| 9,949,651 B2 * | 4/2018 | Stone ..................... | A61B 5/389 |
| 10,945,653 B2 * | 3/2021 | Davie ..................... | A61B 5/08 |
| 10,970,936 B2 * | 4/2021 | Osborn ................ | A61B 5/0077 |
| 2002/0156399 A1 * | 10/2002 | Kanderian ............. | A61B 5/224 600/587 |
| 2004/0054273 A1 * | 3/2004 | Finneran ................ | A61B 5/389 600/393 |
| 2005/0113703 A1 * | 5/2005 | Farringdon .......... | A61B 5/0205 600/509 |
| 2006/0100540 A1 * | 5/2006 | Gozani ................ | A61B 5/1106 600/554 |
| 2008/0033259 A1 * | 2/2008 | Manto .................. | A61B 5/1101 600/301 |
| 2012/0022347 A1 * | 1/2012 | Liu ........................ | A61B 5/061 600/316 |

(Continued)

OTHER PUBLICATIONS

Baker (2018) Clin. Neurophysiol. 129, 1455-1456.
(Continued)

*Primary Examiner* — May A Abouelela
(74) *Attorney, Agent, or Firm* — McDonnell Boehnen Hulbert & Berghoff LLP

(57) ABSTRACT

The present disclosure provides methods for diagnosing and determining the disease progression of neurodegenerative disorders in patients using neurophysiological biomarkers.

12 Claims, 9 Drawing Sheets

(56) References Cited

U.S. PATENT DOCUMENTS

| | | | | |
|---|---|---|---|---|
| 2013/0046715 A1* | 2/2013 | Castermans | ......... | A61B 5/1038 706/12 |
| 2013/0116514 A1* | 5/2013 | Kroner | ................ | A61B 5/333 600/301 |
| 2013/0289434 A1* | 10/2013 | Chou | ................ | A61B 5/394 600/546 |
| 2013/0317648 A1* | 11/2013 | Assad | ................ | B25J 9/1694 700/258 |
| 2014/0088452 A1* | 3/2014 | Ishikawa | ............ | A61B 5/6813 600/546 |
| 2014/0200432 A1* | 7/2014 | Banerji | ............ | A63B 21/4017 600/383 |
| 2015/0165269 A1* | 6/2015 | Herrala | ............ | A63B 24/0062 482/8 |
| 2015/0223743 A1* | 8/2015 | Pathangay | ............ | A61B 5/18 600/301 |
| 2018/0193644 A1* | 7/2018 | Annoni | ............ | A61N 1/0534 |
| 2018/0235503 A1* | 8/2018 | Derkx | ............ | A61B 5/7246 |
| 2018/0296112 A1* | 10/2018 | Girouard | ............ | A61B 5/389 |
| 2020/0000433 A1* | 1/2020 | Frich | ............ | A61B 5/389 |
| 2020/0353239 A1* | 11/2020 | Daniels | ............ | A61B 5/296 |

OTHER PUBLICATIONS

Baker et al. (1997) J. Physiol. 501, Pt 1, 225-41.
Farmer et al. J. Physiol. 470, 127-55 (1993).
Fisher et al. (2012) Brain 135, 2849-64.
Halliday et al. (1995) Progr. Biophys Mol Biol.
Issa et al. (2017) Muscle Nerve 55:862-68.
Norton et al. (2006) J. Neurophysiol 95, 2580-2589.
Proudfoot et al. (2018) Clin. Neurophysiol. 129, 1479-1489.
Rosenberg et al. (1989) Progt. Biophys. Mol. Biol. 53:1031.
Semmler et al. (2013) Acta. Physiol 208:362-375.

* cited by examiner

NEUROPHYSIOLOGICAL BIOMARKERS FOR NEURODEGENERATIVE DISORDERS

CROSS-REFERENCE TO RELATED APPLICATIONS

This application claims priority to U.S. Provisional Patent Application No. 62/727,362, filed Sep. 5, 2018, the disclosure of which is hereby incorporated by reference in its entirety.

BACKGROUND OF THE INVENTION

Field of the Invention

The present disclosure provides methods for diagnosing and determining disease progression of amyotrophic lateral sclerosis (ALS) and other neurodegenerative disorders. More particularly, the present disclosure relates to methods for diagnosing and determining the disease progression of neurodegenerative disorders in patients using neurophysiological biomarkers.

Description of the Related Art

Amyotrophic lateral sclerosis (ALS) is a paralyzing fatal disease caused by progressive degeneration of motor neurons in the brain and spinal cord. Between 2 and 5 people per 100,000 people over the age of 50 will develop ALS in a year. The median survival rate is from 20 months to 48 months. Approximately 20,000 people in the United States have ALS at any given time. However, treatment options are limited, and several new drug therapies are under development.

The diagnosis of ALS is based on signs and symptoms of progressive weakness with signs of lower motor neuron (LMN) and upper motor neuron (UMN) abnormality and with the exclusion of disease mimics. LMN involvement can be confirmed by electromyography (EMG). Therapy development for ALS is hindered, in part, by the lack of quantitative biomarkers for disease progression. There is a need for reliable biomarkers for UMN dysfunction, which is routinely determined on clinical grounds.

SUMMARY OF THE INVENTION

The embodiments as described herein provide a quantitative and objective measure of disease progression in patients with ALS and other neurodegenerative disorders. The embodiments described herein also provide an assessment of whether upper motor neuron control of muscles is normal or dysfunctional.

One embodiment provides a method for diagnosing a neurodegenerative disorder in a subject, the method comprising: i) obtaining surface electromyographic (EMG) signal data from a pair of muscles in the subject; ii) processing the EMG signal data to determine an intermuscular coherence (IMC) phase of response between the pair of muscles across a frequency range; and iii) analyzing variability of the IMC phase of response between the pair of muscles across the frequency range to determine a phase variance value, wherein the phase variance value indicates whether the subject suffers from a neurodegenerative disorder. In some embodiments, the frequency range is about 5 Hz to about 80 Hz, or about 20 Hz to about 40 Hz, or about 10 Hz to about 50 Hz.

In some embodiments, the method for diagnosing a neurodegenerative disorder in a subject further comprises determining an intermuscular coherence (IMC) value, wherein the IMC value comprises an average IMC magnitude of the response between the pair of muscles across the frequency range. In other embodiments, the method further comprises causing a display interface to display the phase variance value plotted against the IMC value.

In some embodiments, a phase variance value of between about 0.2 to about 1.2 and an IMC value of equal to or less than about 0.023 indicates that the subject suffers from a neurodegenerative disorder. In other embodiments, a phase variance value of between about 0 to about 0.6 and an IMC value of greater than about 0.023 indicates that the subject does not suffer from a neurodegenerative disorder. In yet other embodiments, the phase variance value directly correlates to the severity of disease progression.

In some embodiments, the neurodegenerative disorder is amyotrophic lateral sclerosis (ALS), spinocerebellar ataxia, fronto-temporal dementia, or primary lateral sclerosis.

In some embodiments, the subject is an asymptomatic relative of a subject with a neurodegenerative disorder. In other embodiments, the subject is asymptomatic of a neurodegenerative disorder.

In some embodiments, the pair of muscles includes arm muscles, hand muscles, leg muscles, or respiratory muscles. In other embodiments, the pair of arm muscles is the brachioradialis muscle and the biceps muscle.

In some embodiments, the method for diagnosing a neurodegenerative disorder in a subject further comprises causing a display interface to display a plot of the phase of the response between the pair of muscles across the frequency range.

In some embodiments, the method for diagnosing a neurodegenerative disorder in a subject further comprises causing a display interface to display the phase variance value and an indication when the phase variance value exceeds a predetermined threshold value.

Another embodiment provides a method for monitoring the disease progression of a neurodegenerative disorder in a subject, the method comprising: i) obtaining surface electromyographic (EMG) signal data from a pair of muscles in the subject; ii) processing the EMG signal data to determine an intermuscular coherence (IMC) value, wherein the IMC value comprises an average IMC magnitude of response between the pair of muscles across a frequency range; iii) repeating steps i-ii over time to obtain more than one IMC value; and iv) determining a trend in the IMC values, wherein a decrease in IMC values over time indicates disease progression of the neurodegenerative disorder in a subject.

In some embodiments, the IMC value is measured between a frequency of about 5 Hz and about 80 Hz. In other embodiments, the IMC value is measured between a frequency of about 20 Hz and about 40 Hz.

In other embodiments, the difference in the IMC values is used to calculate a change metric.

In some embodiments, the change metric directly correlates to the severity of disease progression.

In some embodiments, the steps i-ii of the method for monitoring the disease progression of a neurodegenerative disorder in a subject are repeated in daily, weekly, monthly, or yearly intervals. In other embodiments, steps i-ii are repeated every three months.

In some embodiments, the neurodegenerative disorder is amyotrophic lateral sclerosis (ALS), spinocerebellar ataxia, fronto-temporal dementia, or primary lateral sclerosis. In other embodiments, the subject is an asymptomatic relative of a subject with a neurodegenerative disorder. In yet other embodiments, the subject is asymptomatic of a neurodegenerative disorder.

In some embodiments, the pair of muscles includes arm muscles, hand muscles, leg muscles, or respiratory muscles. In other embodiments, the pair of arm muscles is the brachioradialis muscle and biceps muscle.

In some embodiments, the method for monitoring the disease progression of a neurodegenerative disorder in a subject further comprises causing a display interface to display a plot representative of the trend in IMC values over time.

Provided, therefore, are metrics that can be used to diagnose, predict the likelihood of, and determine the disease progression of amyotrophic lateral sclerosis (ALS) and other neurodegenerative diseases in patients. The metrics include, but are not limited to, the variability of the intermuscular coherence (IMC) phase across a frequency range and the changes in IMC over time.

BRIEF DESCRIPTION OF THE DRAWINGS

The accompanying drawings are included to provide a further understanding of the methods and compositions of the disclosure, and are incorporated in and constitute a part of this specification. The drawings illustrate one or more embodiment(s) of the disclosure, and together with the description serve to explain the principles and operation of the disclosure.

FIG. 1A is a graph illustrating that IMC between biceps and brachioradialis was lower in the 20-40-Hz range (highlighted with a gray bar) in patients diagnosed with ALS (n=15) compared with age and gender-matched normal controls (n=15). Error bars indicate standard error of the mean (SEM). FIG. 1B is a scatterplot of IMC averaged over 20-40 Hz from the ALS patients and normal control subjects (open circles: individual subjects; gray diamonds: average IMC for each condition). The dashed line shows the cut-off used to calculate sensitivity and specificity. Sensitivity and specificity were both 87%. Error bars: 95% confidence intervals. (Issa et al. (2017) *Muscle Nerve* 55:862-68).

FIG. 4A, FIG. 4B, and FIG. 4C are plots of IMC amplitude as a function of frequency in normal subjects. FIG. 4D is a plot of the IMC profile averaged across many normal subjects.

DETAILED DESCRIPTION OF THE INVENTION

Figure 1A:
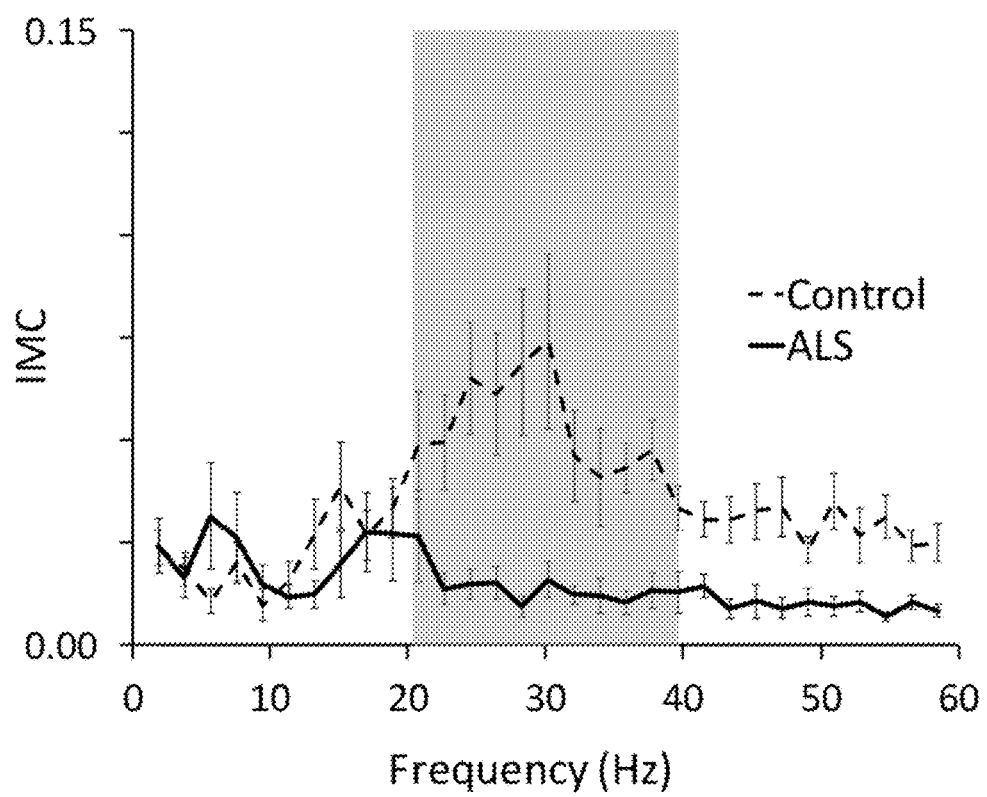
FIGS. 1A-1B illustrates differentiating patients with independently diagnosed ALS from normal control subjects using IMC.

Before the disclosed processes and materials are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used in the specification and the appended claims, the singular forms "a," "an" and "the" include plural referents unless the context clearly dictates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

The embodiments illustratively described herein suitably can be practiced in the absence of any element or elements, limitation or limitations that are not specifically disclosed herein. Thus, for example, in each instance herein any of the terms "consisting," "consisting essentially of," and "consisting of" may be replaced with either of the other two terms, while retaining their ordinary meanings.

Ranges can be expressed herein as from "about" one particular value, and/or to "about" another particular value. As used herein, the term "about" in association with a numerical value means that the numerical value can vary plus or minus by 5% or less of the numerical value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In an embodiment, the subject is a human patient that is suffering from ALS.

In some embodiments, the subject is an asymptomatic relative of a subject with a neurodegenerative disorder (e.g., ALS). In other embodiments, the subject is asymptomatic of a neurodegenerative disorder (e.g., ALS).

As used herein, the term "disease" refers to any condition that is abnormal, such as a disorder or a structure or function that affects part or all of a subject.

As used herein, the term "neurodegenerative disorder" refers to debilitating conditions that result in progressive degeneration and/or death of nerve cells, which causes problems with movement (e.g., weakness, fasciculations, hyper-reflexia, ataxias), or mental functioning (e.g., dementias). Neurodegenerative disorders include, but are not limited to, amyotrophic lateral sclerosis (ALS), spinocerebellar ataxia, including subtypes 1, 2, and 3, fronto-temporal dementia, progressive bulbar palsy, pseudobulbar palsy, primary lateral sclerosis, progressive muscular atrophy, and spinal muscular atrophy.

As used herein, the term "diagnose" refers to determining the identity of a disease or illness by medical examination or to ascertain the cause or nature of a disorder or malfunction from the symptoms.

As used herein, the term "disease progression" or "disease development" refers to a change in the way a disorder or illness affects a subject as it moves from its earliest stages to its peak and then to its resolution. In some embodiments, disease progression refers to the progression of a neurodegenerative disorder, including, but not limited to ALS. Development of a neurodegenerative disorder can be detectable and assessed using the methods described herein. However, development also refers to disease progression that may be undetectable to a medical practitioner during a routine exam. For purposes of these embodiments, the terms "development" or "progression" refers to the biological course of the disease state. "Development" includes occurrence, recurrence, and onset. As used herein "onset" or "occurrence" of a neurodegenerative disorder includes initial onset and/or recurrence.

As used herein, the term "neurophysiological biomarker" refers to electrically measured properties of neurons, glia, muscles, and networks that can be used to diagnose, and/or determine the disease progression of a subject with a neurodegenerative disorder. Examples of neurophysiological biomarkers for neurodegenerative diseases (e.g., ALS) include, but are not limited to, an IMC value (e.g., the average IMC magnitude over a frequency range), a full IMC profile, which would be the full plot of IMC magnitude over the frequency range, IMC value as a function of age and/or gender, phase variance value, the change metric in IMC value over time, and IMC magnitude.

IMC is a measure of correlation in activity between two muscles during a motor task, and represents the shared input to the muscles from the upper motor neurons in the motor cortex. (Fisher et al. (2012) Brain 135, 2849-64; Issa et al. (2017) Muscle Nerve 55:862-68). IMC is measured over different frequency ranges of muscle activity, and coherence in the range of 15-40 Hz (beta-to-gamma frequencies) has been shown to represent input from upper motor neurons specifically. (Fisher et al. (2012) Brain 135, 2849-64; Farmer et al. J. Physiol. 470, 127-55 (1993); Baker et al. (1997)J. Physiol. 501, Pt 1, 225-41; Proudfoot et al. (2018) Clin. Neurophysiol. 129, 1479-1489). The measurement of IMC is quick, non-invasive, painless, requires only equipment found in standard clinical neurophysiology labs, and is easy to perform without extensive technical expertise. (Issa et al. (2017) Muscle Nerve 55:862-68; Baker (2018) Clin. Neurophysiol. 129, 1455-1456).

In view of the present disclosure, the methods and compositions described herein can be configured by the person of ordinary skill in the art to meet the desired need. In general, the disclosed materials, methods, and apparatuses provide improvements in diagnosing and determining the disease state of neurodegenerative disorders. For example, IMC measured in the frequency range of about 20-40 Hz ($\beta\gamma$ range) between two muscles (e.g., the biceps and brachioradialis (BC-BR) muscles) during a task (e.g., holding the arm bent at the elbow) can distinguish between patients with established ALS and normal subjects. Furthermore, EMG signals have a different phase relationship in patients with ALS as compared with normal patients. Additionally, IMC (e.g., coherence between biceps and brachioradialis muscles BCBR-IMC) decreases during the first two years of the disease and IMC (e.g., BCBR-IMC) that was repeated at intervals demonstrates that the metric decreases monotonically with disease duration.

Thus, one aspect of the disclosure provides methods for diagnosing a neurodegenerative disorder in a subject, the method comprising: i) obtaining surface electromyographic (EMG) signal data from a pair of muscles in the subject; ii) processing the EMG signal data to determine an intermuscular coherence (IMC) phase of response between the pair of muscles across a frequency range; and iii) analyzing variability of the IMC phase of the response between the pair of muscles across the frequency range to determine a phase variance value, wherein the phase variance value indicates whether the subject suffers from a neurodegenerative disorder.

As used herein, the term "electromyographic (EMG)" refers to a technique for evaluating and recording the electrical activity produced by skeletal muscles. EMG is performed using an electromyograph to produce a record called an electromyogram. An electromyograph detects the electric potential generated by muscle cells when these cells are electrically or neurologically activated. The signals can be analyzed to detect medical abnormalities, activation level, or recruitment order, or to analyze the biomechanics of human or animal movement.

As used herein, the term "processing" refers to the collection and manipulation of items of data to produce meaningful information. Data processing can be achieved by executing program instructions (e.g., as part of a software program) on a computing device. More specifically, a software program may receive and process EMG sensor data to determine characteristics of neurodegenerative disease state in a patient. In some examples, the software program can receive user input data from an input interface (e.g., a keyboard or touchscreen device), through which patient characteristics such as sex, age, known disease state (e.g., normal control, ALS, other, unknown pathology), added load (e.g., none (gravity), 3 pounds, 5 pounds, or other weight), and the particular clinical EMG machine from which the EMG signal data was collected can be inputted. In some examples, the software program may also include instructions to control the output of a display interface (10) (e.g., a computer screen). In some examples, the software program allows the practitioner to select different system outputs (e.g., a "verbose" or "quiet" output) such that selecting "verbose" allows a practitioner to see many analysis steps (including phase and IMC plots, EMG amplitude measures, etc.) while selecting "quiet" allows the practice to visualize only the calculated IMC-βγ with an assessment of "normal" or "abnormal."

In other examples, the software program may also include visualization of subsets extracted from the original EMG traces that are used for calculation, visualization of EMG power spectra to assess for signal quality, and visualization of artifact rejection based on amplitude thresholds. In some examples, the software writes output to a file that can be subsequently used for post-hoc analysis.

In other examples, the software interface may be updated to add support for additional EMG machines and implement specific metrics, such as the change metric, age-adjusted ALS risk, and symptom duration-adjusted ALS risk.

On one window of the display interface (10), an IMC value can be determined and displayed with an indication whether the value was in the normal or abnormal range. An IMC value equal to or lower than about 0.023 is an indication that the patient has abnormal upper motor neuron function, as would be found in ALS. In an embodiment, the threshold IMC value is about 0.020, 0.021, 0.023, 0.025, 0.027, 0.029, 0.030, or lower. On another window of the display interface, IMC Magnitude may be plotted as a function of frequency (Hz). On yet another window of the display interface, IMC phase may be plotted as a function of frequency (Hz). On another window, calculated metrics include a phase variance value or an IMC-βγ change metric, and may be determined and displayed with an indication when the phase variance value exceeds a predetermined threshold value or whether the change metric is consistent with clinical worsening or improvement.

As used herein, the term "intermuscular coherence (IMC)" refers to the coherence calculated between 2 signals when both signals are measured at discrete frequencies. It is calculated in the frequency domain and is scaled between 0 and 1, where a value of 0 indicates that 2 signals vary independently, and a value of 1 indicates that one signal can be perfectly predicted by a linear transformation of the other signal. When applied to EMG, 2 muscle fibers that are driven at a specific frequency would have high coherence at that frequency. As used herein, an "intermuscular coherence (IMC) value" (also referred to herein as "IMC βγ" or "IMC bg") comprises an average IMC magnitude of the responses between the two muscles across the frequency range, typically 20 to 40 Hz.

Intermuscular coherence (IMC) analysis quantifies the similarity in EMG activity of a pair of muscles in a certain frequency domain. This method detects frequency components that are common in the 2 sets of EMG signals as a result of common input to the LMNs, such as oscillatory activity originating from the motor cortex. (Farmer et al. (1993) J. Physiol 470:127-155; Baker et al. (1997) *J. Physiol* 501:225-241). In some embodiments, the IMC analysis is performed in a frequency range of about 5 Hz to about 80 Hz, about 10 Hz to about 80 Hz, about 10 Hz to about 70 Hz, about 10 Hz to about 50 Hz, about 20 Hz to about 70 Hz, about 20 Hz to about 60 Hz, or about 20 Hz to about 40 Hz.

As used herein, the term "intermuscular coherence (IMC) phase of response" refers to a phase difference between activity in the two muscles, calculated at individual frequencies between 5 and 60 Hz. The phase difference between the activity of two muscles can vary from about $-\pi$ to about $+\pi$ ($\pi$=pi, $\pi$~3.141592) at each frequency measured. The IMC phase of response can be used to calculate the "phase variance value," which refers to the average variability of the IMC phase over a particular frequency range, typically 20 to 40 Hz.

The phase variance metric is calculated as follows: when coherence is calculated between two EMG signals, two outputs are produced (1) the amplitude of the coherence between the signals (e.g., how well one signal predicts the other signal) and (2) the average phase difference between the signals (e.g., how much delay there is between peaks in the signals). Each of these outputs varies by frequency. The phase variance quantifies how stable the phase difference (lag between the signals) is across frequencies between 20 and 40 Hz. Phi(f)=the average phase difference between the EMG signals at frequency "f." Phase variance=standard deviation of Phi(f) where f ranges from 20 to 40 Hz. If the phase difference between two muscles is constant at all frequencies between 20 and 40 Hz, the phase variance is 0. If the phase difference between the muscle activity varies substantially across the frequency band, the phase variability measure will be large. The IMC phase variance value can range between about 0 and about $\pi/2$. In some embodiments, the IMC phase variance value is calculated between a frequency range of about 5 Hz to about 80 Hz, about 10 Hz to about 80 Hz, about 10 Hz to about 70 Hz, about 10 Hz to about 50 Hz, about 20 Hz to about 70 Hz, about 20 Hz to about 60 Hz, or about 20 Hz to about 40 Hz. Example IMC phase variance values that may be computed for a patient include (approximately) 0, 0.1, 0.2, 0.3, 0.4, 0.5, 0.6, 0.7, 0.8, 0.9, 1.0, 1.1, or 1.2.

The phase variance value as described herein can be used to diagnose and determine the disease progression in a subject suffering from a neurodegenerative disorder, including, but not limited to, ALS. In some embodiments, a phase variance value of between about 0.2 to about 1.2, about 0.3 to about 1.1, about 0.3 to about 0.9, about 0.3 to about 0.8, about 0.4 to about 1.1, about 0.4 to about 1.0, about 0.5 to about 1.0, about 0.6 to about 1.0, about 0.7 to about 1.0, about 0.8 to about 1.0, about 0.9 to about 1.1, about 0.3 to about 1.2, about 0.4 to about 1.2, about 0.5 to about 1.2, about 0.6 to about 1.2, about 0.7 to about 1.2, about 0.8 to about 1.2, or about 0.9 to about 1.2, and an IMC value of equal to or less than about 0.023 indicates that the subject suffers from a neurodegenerative disorder. In some embodiments, a phase variance value of between about 0 to about 0.8, about 0 and about 0.7, about 0 and about 0.6, about 0.1 and about 0.6, about 0.1 and about 0.5, about 0.2 and about 0.5, or about 0.3 and about 0.5, and an IMC value greater than about 0.023 indicates that the subject does not suffer from a neurodegenerative disorder. An example patient may have a computed phase variance value of (approximately) 0, 0.1, 0.2, 0.3, 0.4, 0.5, 0.6, 0.7, 0.8, 0.9, 1.0, 1.1, or 1.2 and a computed IMC value of (approximately) about 0.020, 0.021, 0.023, 0.025, 0.027, 0.029, 0.030, or lower.

In some embodiments, the phase variance value directly correlates to the severity of the disease progression.

As used herein, the term "pair of muscles" refers to two different muscles on the subject. In some embodiments, the muscle pair is a pair of arm muscles, including but not limited to the brachioradialis muscle and the biceps muscle. In other embodiments, the muscle pair includes a pair of hand muscles, leg muscles, or respiratory muscles (e.g., chest wall muscles).

Another embodiment provides methods for monitoring the disease progression of a neurodegenerative disorder in a subject, the method comprising: i) obtaining surface electromyographic (EMG) signal data from a pair of muscles in the subject; ii) processing the EMG signal data to determine an intermuscular coherence (IMC) value, wherein the IMC value comprises an average IMC magnitude of response between the pair of muscles across a frequency range; iii) repeating steps i-ii over time to obtain more than one IMC value; and iv) determining a trend in the IMC values, wherein a decrease in IMC values over time indicates disease progression of the neurodegenerative disorder in a subject. In some embodiments, the IMC value is determined by measuring and averaging an IMC magnitude between a frequency of about 5 Hz to about 80 Hz, about 10 Hz to about 80 Hz, about 10 Hz to about 70 Hz, about 10 Hz to about 50 Hz, about 20 Hz to about 70 Hz, about 20 Hz to about 60 Hz, or about 20 Hz to about 40 Hz. In an embodiment an abnormal IMC value can be about 0.020, 0.021, 0.023, 0.025, 0.027, 0.029, 0.030, or lower.

In some embodiments, the difference in the IMC values is used to calculate a change metric. In other embodiments, the change metric directly correlates to the severity of the disease progression.

In some embodiments, variability of the IMC phase across frequencies and/or changes in IMC values over time is used to predict the likelihood of ALS or another upper motor neuron disease. The methods disclosed herein are used to obtain a subject's IMC, which would then be used as the subject's initial or baseline IMC value. The baseline IMC value would then be compared to future IMC values measured from the subject. Changes in IMC values over time, and/or variability of the IMC phase is then used to predict the likelihood of the subject advancing to ALS or another upper motor neuron disease.

In some embodiments, steps i-ii of a method for monitoring the disease progression of a neurodegenerative disorder in a subject are repeated in daily, weekly, monthly, or yearly intervals. In other embodiments, steps i-ii are repeated every three months.

In some embodiments, the software program processes EMG signal data to determine a series of intermuscular coherence (IMC) values over time for a patient and causes a display interface (10) to display a plot representative of the trend in IMC values over time.

Some example methods may be performed by a computing device that has been programmed to perform one or more functions. The computing device may be communicatively coupled to one or more other devices, such as an EMG machine, an input interface, and/or a display interface (10). Each function performable by the computing device may be represented by a module, a segment, or a portion of program code, which includes one or more instructions executable by the computing device (or a processor thereof) for implementing specific logical functions or steps in the process. The program code can be stored on any type of computer-readable medium, for example, such as a storage device including a disk or hard drive. The computer-readable medium can include non-transitory computer-readable medium, for example, such as computer-readable media that stores data for short periods of time like register memory, processor cache and random access memory (RAM). The computer-readable medium can also include non-transitory media, such as secondary or persistent long term storage, like read only memory (ROM), optical or magnetic disks, compact-disc read only memory (CD-ROM), for example. The computer-readable medium can also be any other volatile or non-volatile storage systems. The computer-readable medium can be considered a computer-readable storage medium, for example, or a tangible storage device.

Certain aspects of the disclosure are now explained further via the following non-limiting examples.

EXAMPLES

Example 1: IMC Dy Can Distinguish ALS Patients from Normal Controls

To determine whether the degree to which co-activated muscles are driven at the same frequency can discriminate between patients with ALS and normal subjects, coherence was used as a measure of shared drive to a pair of muscles, as described in Issa et al. (2017) *Muscle Nerve* 55:862-868, which is incorporated by reference herein in its entirety.

Subjects. Patients with ALS were recruited from the University of Chicago multidisciplinary ALS clinic and had been clinically diagnosed with the disease. Twelve of 15 patients included in the study had definite ALS according to revised El Escorial criteria. The remaining 3 patients had progressive denervation in multiple myotomes without clinical presence of UMN signs at the time of the study and, as ALS mimics were excluded, they were diagnosed with an LMN variant of ALS. One of the 3 subjects subsequently progressed to have UMN signs and therefore was reclassified as definite ALS. Gender- and age-matched (within 3 years) control subjects were recruited from faculty, staff, spouses of clinic patients, or neurology clinic patients without active neuromuscular disease. The control subjects had no known neurological disease, except for 1 who was in asymptomatic remission for >5 years from chronic inflammatory demyelinating polyneuropathy (CIDP) and 1 who had a small orbitofrontal meningioma and was on levetiracetam. The 30-min testing session (which included the consent process, set-up, instructions, and testing) took place during a regular outpatient clinic visit. The institutional review board of University of Chicago Biological Science Division approved this study before data collection, and all subjects (ALS patients and normal control subjects) provided informed written consent before participation.

Surface EMG. Paired surface EMG recordings were made from the BC-BR muscles of the stronger arm in ALS patients, and the dominant arm in control subjects. The BC-BR muscle pair was selected for IMC measurements, because they are large (allowing easy electrode placement) and generate consistent surface EMG activity with a simple task, but also because a previous study showed consistent IMC when they were co-activated. (Semmler et al. (2013) *Acta. Physiol* 208:362-375). The task of holding the forearm steady and parallel to the floor is simple to perform and can be carried out by most ALS patients, even those with significant weakness. Reference and recording electrodes (Nicolet bipolar disk bar electrodes; Natus Medical, Inc., Pleasanton, Calif.) were separated by 3 cm, and a ground electrode was placed on the volar surface of the wrist. Waveforms were recorded using the Neuroscan Neurophysiology System (Version 4.3; Compumedics Neuroscan, Charlotte, N.C.). Signals were sampled digitally at 500 Hz, high-pass filtered at 1 Hz, low-pass filtered at 100 Hz, and notch-filtered at 60 Hz. Subjects were instructed to hold the arm at their side with the elbow flexed at 90 degree, with the forearm semipronated and parallel to the floor. Two or 3 epochs of approximately 30 s each of flexion were recorded, totaling approximately 1.5-2.5 min. Between epochs, the arm was rested for approximately 30 s in pronation. Transient high amplitude EMG discharges that occurred with arm positioning at the beginning and end of an epoch were excluded from analysis.

IMC Calculation and Statistical Analysis.

IMC was calculated during the 30-s epochs of active elbow flexion using sequential ~0.5-s subsets (256 points). The IMC calculation was implemented using the IDL programming language employing the cross_spectrum.pro algorithm described by Vaughan (www.star.le.ac.uk/_sav2/idl/cross_spectrum.pro/). It was calculated between the 2 EMG signals at frequency co using the relationship:

$$IMC(\omega) = \frac{|G_{xy}(\omega)|^2}{G_{xx}(\omega)G_{yy}(\omega)}$$

where IMC(w) is the coherence at frequency ω; Gxx and Gyy are the auto-spectra of x and y, respectively; and Gxy is the cross-spectrum of signals x and y. (Rosenberg et al. (1989) *Progt. Biophys. Mol. Biol.* 53:1031; Halliday et al. (1995) *Progr. Biophys Mol Biol*).

Results

Intermuscular coherence was calculated from surface EMG signals recorded from the BC-BR pair of the 15 ALS patients and 15 age- and gender-matched control subjects.

IMC varied by frequency (FIG. 1), as has been previously demonstrated in different muscle pairs. (Farmer et al. (1993) *J. Physiol* 470:127-155; Baker et al. (1997)*J. Physiol* 501: 225-241; Fisher et al. (2012) *Brain* 135:2849-64). On average, IMC was greater in normal subjects than in ALS patients at most frequencies <60 Hz. In normal subjects there was a peak of BC-BR IMC between 20 and 40 Hz (βγ range), with the average peak frequency around 30 Hz (FIG. 1). The difference in IMC between normal subjects and ALS patients appeared most pronounced in this βγ frequency range in the average profiles shown in FIG. 1A.

Figure 1B:
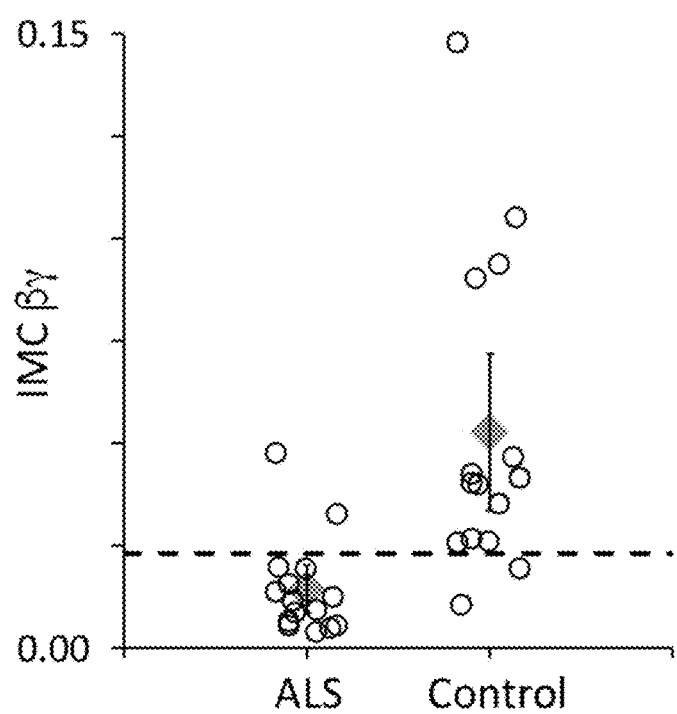

IMC-βγ in ALS patients was significantly lower than in normal control subjects [ALS, 0.014±0.006 (mean±2×SEM) vs. control, 0.053±0.019; U=23, P<0.01; FIG. 1]. To calculate the sensitivity and specificity of this test, a cut-off value of 0.023 was used (dashed line in FIG. 1B). With this cut-off, the IMC-βγ had a sensitivity of 87% and specificity of 87% for distinguishing between ALS patients and normal subjects.

Not only was the IMC-βγ lower in magnitude for ALS patients than normal controls, but the variability was also less within the ALS group. The standard deviation of IMC-βγ was 0.011 for the ALS group and 0.037 for the control group.

This study demonstrates that IMC measured in the frequency range of 20-40 Hz (βγ range) between the biceps and brachioradialis (BC-BR) muscles during a task of holding the arm bent at the elbow can distinguish between patients with established ALS and normal subjects.

Example 2: Software to Diagnose and/or Determine the Disease Progression of ALS in a Clinical Setting To further provide a quantitative and objective measure of disease progression in patients with ALS and other neurodegenerative diseases, a software program may be used to calculate an IMC value from EMG signal data, as well as display IMC magnitude and IMC phase plots and other metrics of disease state and progression.

Figure 2:
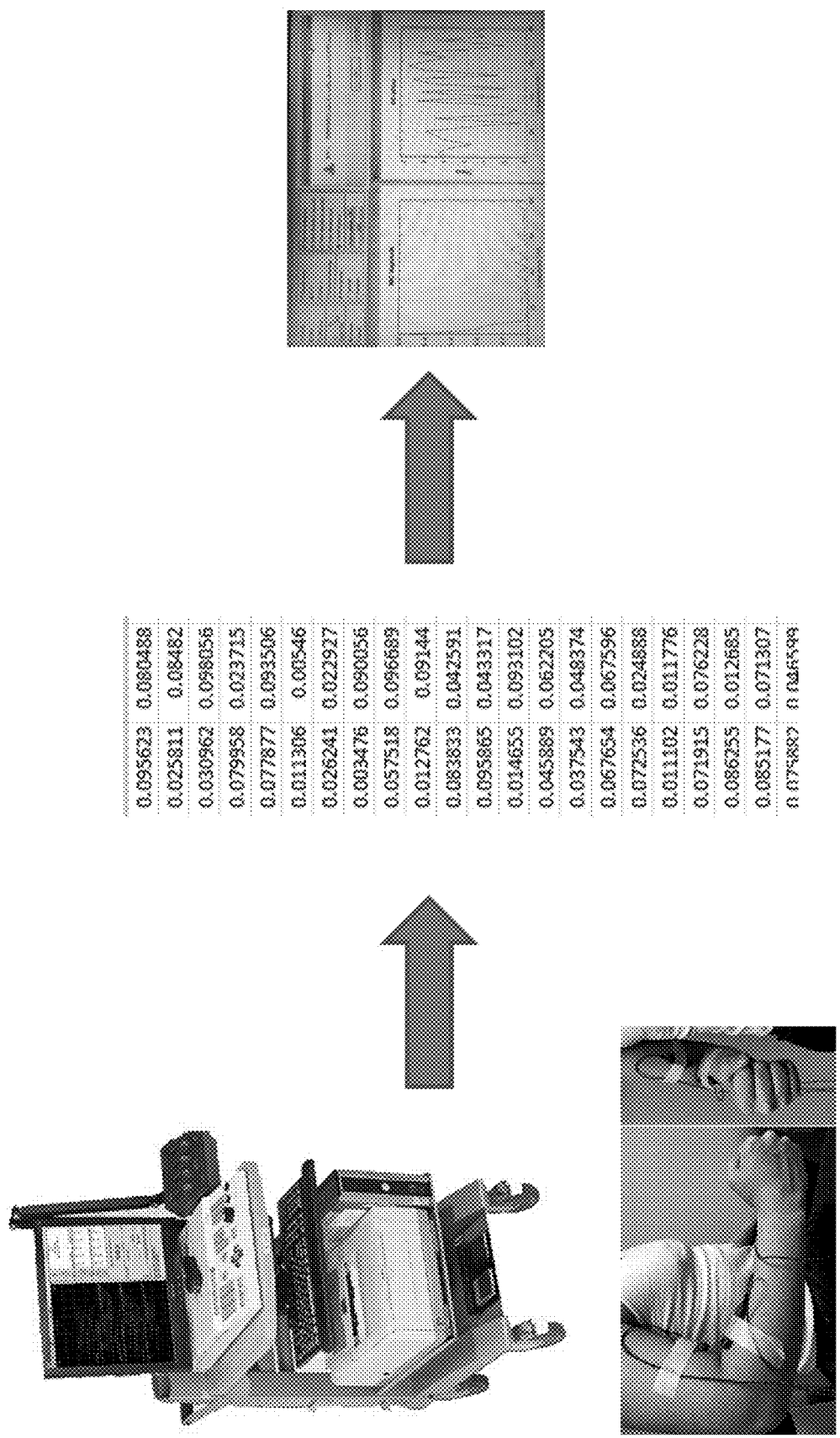
FIG. 2 is a schematic illustrating the general process of how the disease state of a neurodegenerative disorder (e.g., ALS) is measured and determined. First, data is acquired through standard clinical EMG systems, then the EMG signal data is output to a text file, followed by importing the data into a software program that analyzes the surface EMG signals and displays measures of disease state and progression.

The general process to determine disease state of a neurodegenerative disorder is described as follows and shown in the schematic of FIG. 2. EMG signal data was measured from a pair of arm muscles (brachioradialis and biceps muscles) in patients holding the arm bent at the elbow using standard EMG machine (as described in Example 1). Then, the EMG signals were analyzed using a software program to calculate a metric of inter-muscular coherence. Finally, a determination of whether the value of this metric falls in the normal range or the abnormal range based on both theoretical considerations and the distribution of values in normal subjects and values in patients with ALS was made based on the software output display information.

Figure 3:
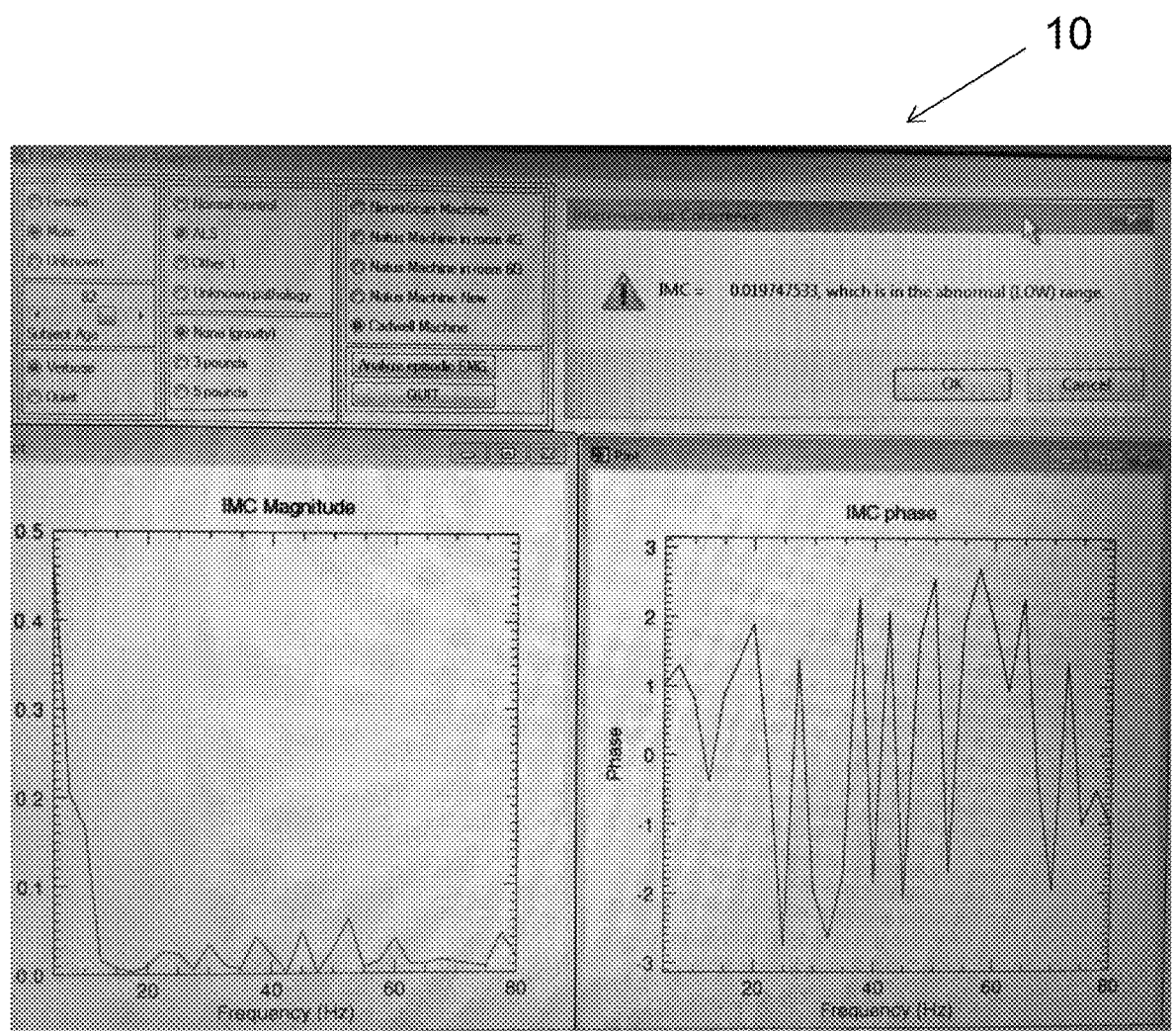
FIG. 3 illustrates a representative computer display interface (10), including a menu where patient characteristics and information regarding the clinical system used to collect EMG signal data can be inputted (upper left window), a plot of IMC Magnitude across a frequency range (lower left window), an IMC value and an indication if the IMC value falls above or below a predetermined threshold value (upper right window), and a plot of IMC phase across a frequency range (lower right window).

As further illustrated in FIG. 3, patient characteristics such as sex, age, known disease state (e.g., normal control, ALD, other, unknown pathology), added load (e.g., none (gravity), 3 pounds, 5 pounds), and the particular clinical EMG machine that the EMG signal data was collected was inputted via an input interface. The practitioner also selected a "verbose" output, which allowed the practitioner to see many analysis steps (including phase and IMC plots, EMG amplitude measures, etc.). The software program determined and displayed an IMC value on a display interface along with an indication whether the value was in the normal or abnormal range. An IMC value equal to or lower than 0.023 indicated that the patient has ALS. As shown in FIG. 3, the patient's IMC value was 0.0197475333, which was in the abnormal (LOW) range.

This threshold IMC βγ value of 0.023 for an indication of ALS may change as more data is collected.

Figure 4A:
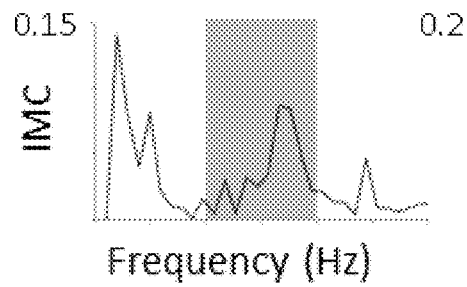
FIGS. 4A-4D illustrates full IMC profiles of normal subjects.
Figure 4B:
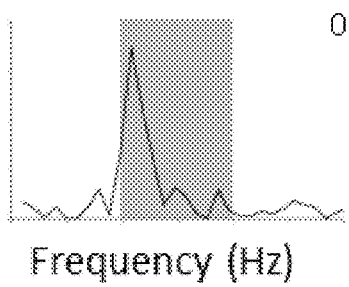
Figure 4C:
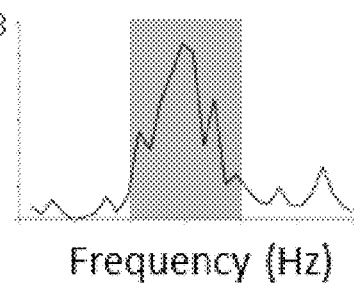
Figure 4D:
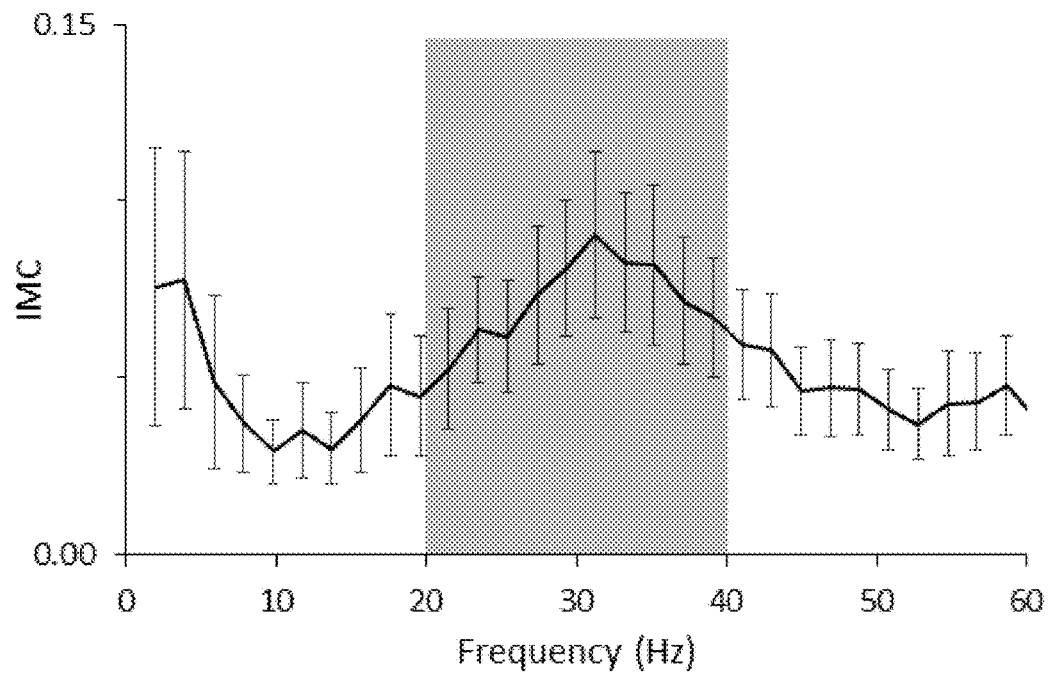

The broad distribution of IMC values among normal subjects, along with the qualitatively different IMC profiles found in some weak patients, suggests that a single numeric value should not be used without reference to the full IMC profiles. The "full IMC profile" refers to the plot of IMC amplitude as a function of frequency. The IMC beta-gamma is the average IMC between 20 and 40 Hz, and as a simple measure this works well. However, because there is variability between individuals, it can be informative to look at the entire profile to see if there is any coherence anywhere. Examples of the variability among normal subjects (FIGS. 4A-4C) and the average IMC profile across many normal subjects (FIG. 4D) are shown.

Figure 5:
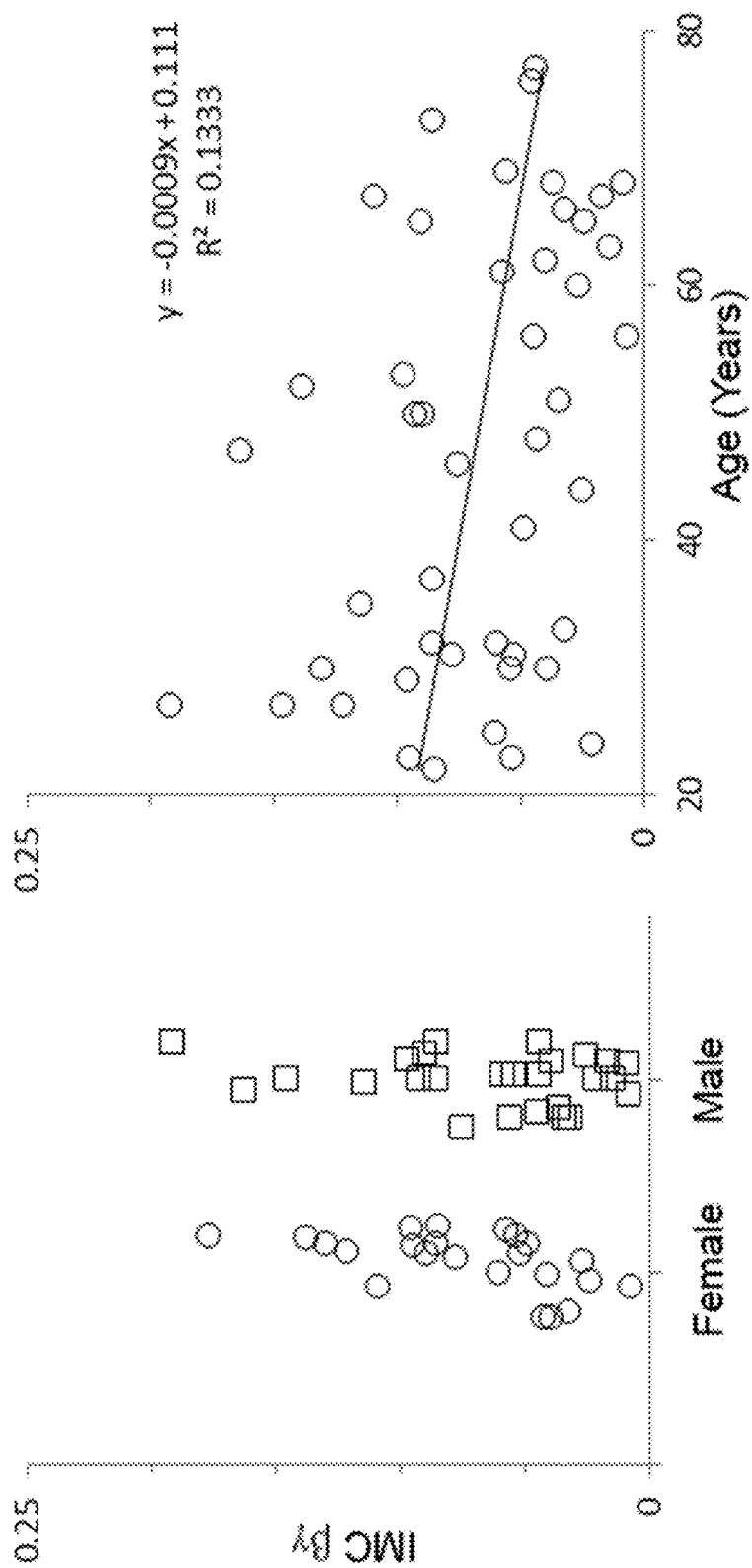
FIG. 5 is a scatter plot of IMC averaged over 20-40 Hz that shows the variability in IMC $\beta\gamma$ by sex and age in normal subjects. There was no statistical difference in the distribution of IMC $\beta\gamma$ between males and females (left plot). IMC $\beta\gamma$ tended to decrease with age (right plot).

Additionally, previously collected data indicated that normal IMC βγ has a tendency to decrease with age (FIG. 5). As the normal and ALS distribution is better defined as a function of age, a "probability" of ALS independent of the cutoff value may also be a metric, and different cutoffs values might be used by age. There was no significant difference in IMC by sex.

In another window of the display interface, IMC Magnitude (the full IMC profile) was plotted as a function of frequency (Hz) (FIG. 3).

In yet another window of the display interface, IMC phase was plotted as a function of frequency (Hz) (FIG. 3).

This approach to diagnosing and determining the disease state in patients with ALS is unique and an improvement on existing approaches in several ways. First, it calculates intermuscular coherence from muscles that are innervated by different peripheral nerves. This reduces the chance of spurious coherence due to nerve fibers travelling together in the same peripheral nerve. Second, the method does not require complex movement, precise tension measurements or high loads, and therefore can be performed in patients who are weak or strong and by technicians with minimal training. This differs from prior art that requires precise measurement of muscle tone with complex movements. Third, the initial acquisition of surface EMG signals can be acquired by currently available clinical EMG machines.

This test is a biomarker for quickly and painlessly following the progression of ALS. The diagnosis of ALS may additionally require appropriate clinical findings on physical exam, appropriate findings on standard EMG studies, and ruling out alternative diagnoses with MRI and/or lumbar puncture. IMC would provide supporting data for initial diagnosis, and the ability to objectively monitor progression.

Finally, this test will not be completely specific for ALS, and will be abnormal for other neurodegenerative diseases with upper motor neuron dysfunction (like certain spino-cerebellar ataxias), and can be used in conjunction with other clinical information. Additionally, IMC can be normal in the earliest stages of ALS and decrease with disease progression, and therefore, could be used to monitor disease progression or follow asymptomatic family members of patients with ALS or certain spino-cerebellar ataxias.

Example 3: IMC Phase Variability as a Biomarker for ALS

Figure 6:
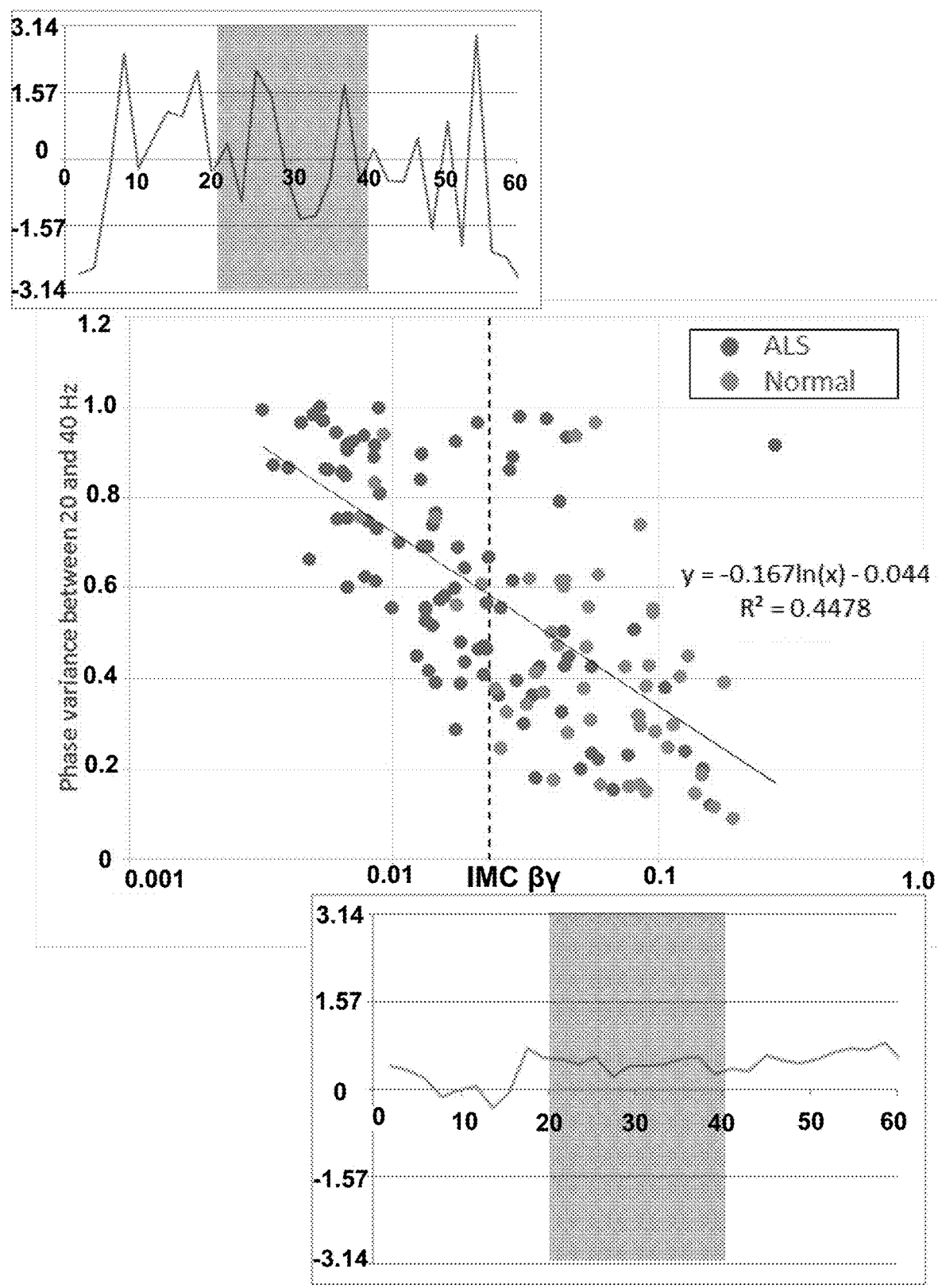
FIG. 6 is a scatter plot showing the phase variance between 20 and 40 Hz as a function of IMC $\beta\gamma$ in ALS and normal patients. The IMC phase plot in the upper left is from an ALS patient and the IMC phase plot in the lower right is from a normal subject.

To determine whether IMC phase variability is a biomarker for ALS, the variability of phase of the responses between the two muscles between 20 and 40 Hz as function of IMC βγ was plotted. As shown in FIG. 6, EMG signals have a different phase relationship in patients with ALS as compared with normal patients. The results indicate that a phase variance value of between about 0.2 to about 1.2 and an IMC βγ value of equal to or less than about 0.023 indicates that the subject suffers from ALS. If the phase difference between two muscles is constant at all frequencies between 20 and 40 Hz, the phase variance is 0 (similar to the low variability seen in the phase plot of the normal subject in FIG. 6). If the phase difference between the muscle activity varies substantially across the frequency band (similar to the phase plot for the ALS patient in FIG. 6), the phase variability measure will be large. Phase variance tends to be higher in patients with ALS than in normal subjects.

Phase variance provides a check of internal consistency for the IMC βγ measure.

Example 4: IMC βγ Over Time as a Biomarker for ALS

Figure 7:
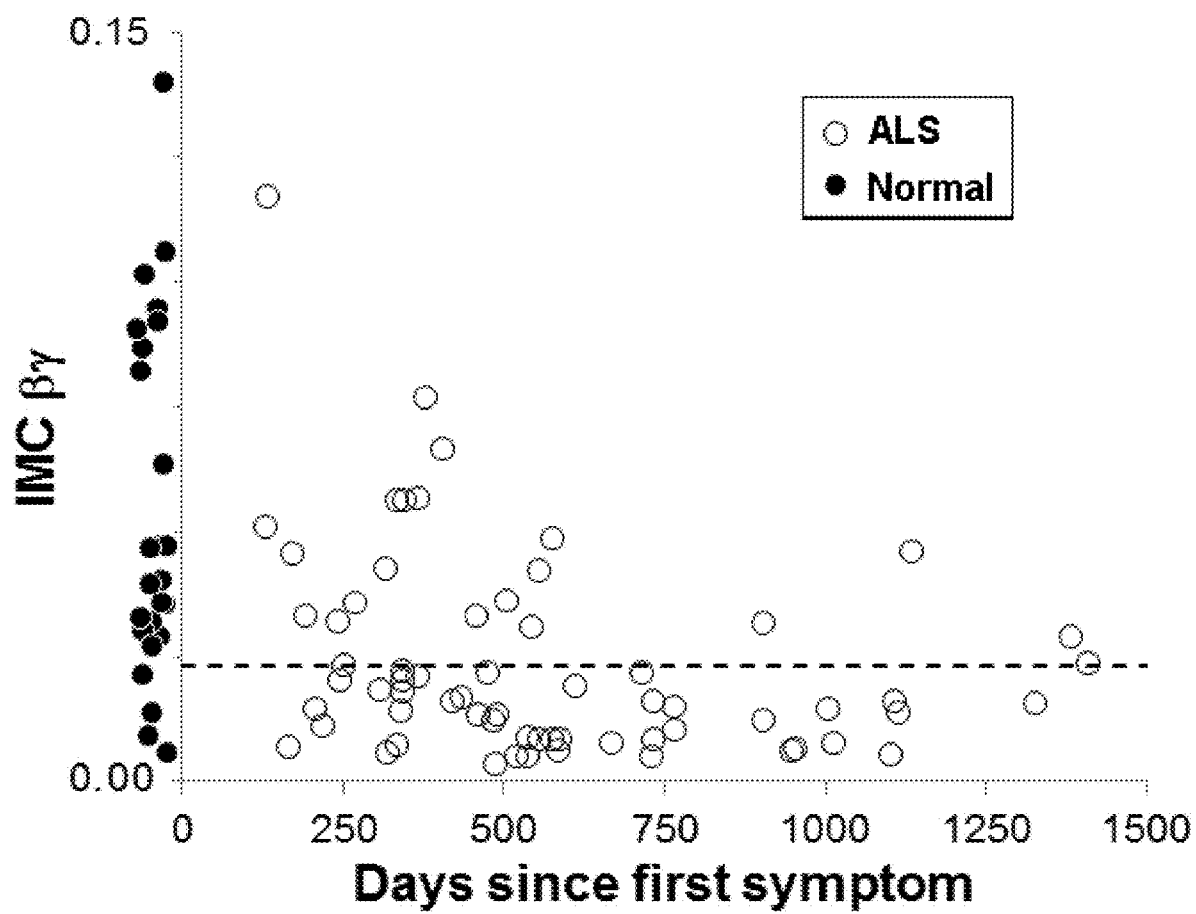
FIG. 7 is a scatter plot of IMC $\beta\gamma$ from ALS patients plotted as a function of time since first symptom onset (open circles). The distribution of IMC values from normal subjects is shown to the left (filled circles).
Figure 8:
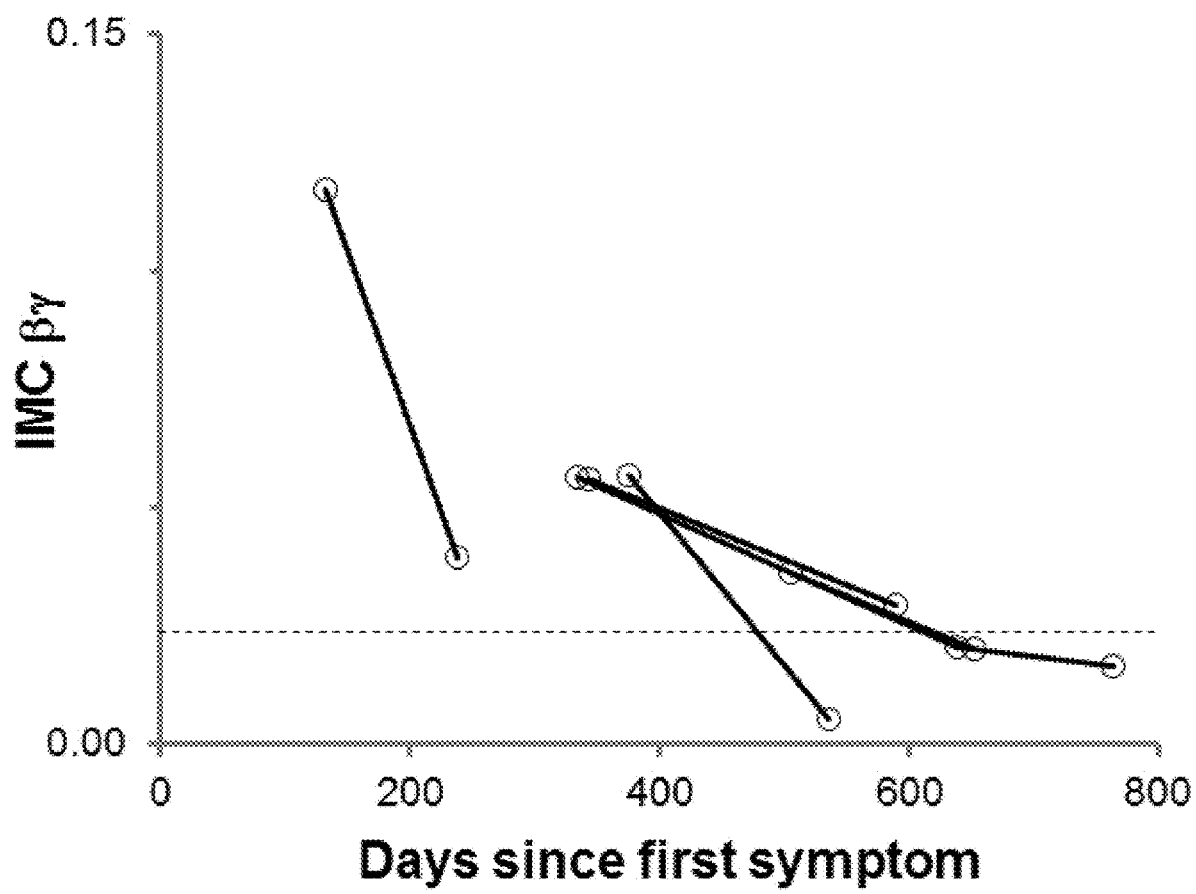
FIG. 8 is a scatter plot of IMC $\beta\gamma$ measured at 3-month intervals in 5 ALS patients. Repeated measurements from the same individual are connected by a line.

To determine whether monitoring the trends in IMC βγ value over time is a biomarker for ALS, the IMC βγ value was plotted as a function of days since the first symptom occurred in patients. The results demonstrate that that the biceps and brachioradialis muscles IMC (BCBR-IMC) decreases during the first two years of the disease (FIG. 7). Furthermore data from subjects in which BCBR-IMC was repeated at 3-month intervals demonstrate that the metric decreases monotonically with disease duration (FIG. 8). This change metric (Δ IMC βγ) can be used to quantify disease progression over time.

Example 5: IMC βγ Can Distinguish Spino-Cerebellar Ataxia Patients from Normal Subjects To determine whether the degree to which co-activated muscles are driven at the same frequency can discriminate between patients with spino-cerebellar ataxia (subtypes 1, 2, and 3) and normal subjects, coherence was used as a measure of shared drive to a pair of muscles, as described in Issa et al. (2017).

Intermuscular coherence was calculated from surface EMG signals recorded from the BC-BR pair in 74 spino-cerebellar ataxias patients and 74 control subjects.

Figure 9:
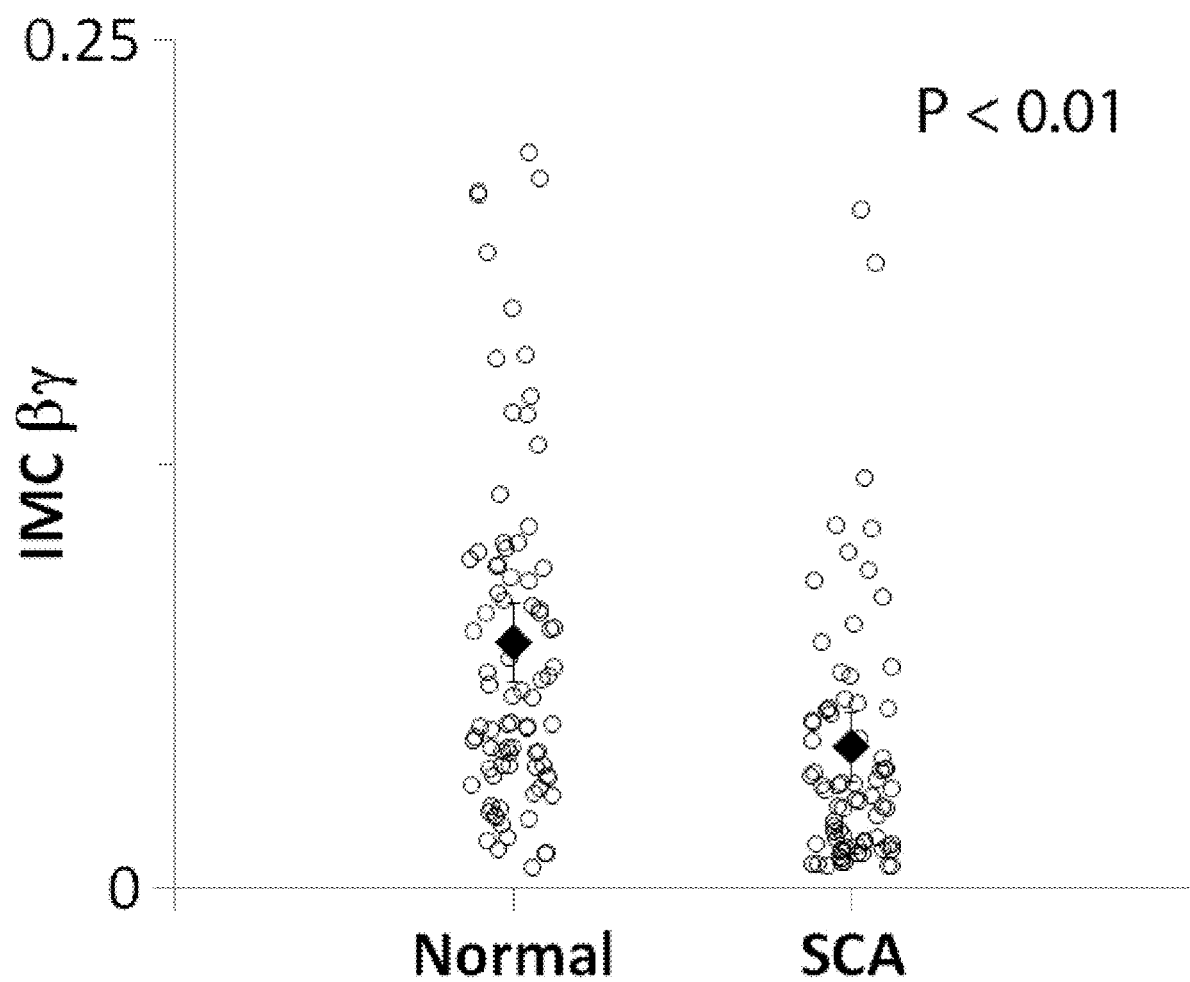
FIG. 9 is a scatterplot of IMC averaged over 20-40 Hz from patients with spino-cerebellar ataxia (subtypes 1, 2, and 3) and normal control subjects. The IMC of the two populations are statistically different with a $P<0.01$.

IMC-βγ in spino-cerebellar ataxia patients was significantly lower than in normal control subjects (spino-cerebellar ataxia, 0.042±0.010 (mean±2×SEM) vs. control, 0.072±0.012; P<0.01; FIG. 9).

This study demonstrates that IMC measured in the frequency range of 20-40 Hz (βγ range) between the biceps and brachioradialis (BC-BR) muscles during a task of holding the arm bent at the elbow can distinguish between patients with spino-cerebellar ataxia (subtypes 1, 2, and 3) and normal subjects.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:

1. A method for diagnosing a neurodegenerative disorder in a subject, the method comprising:
   i) obtaining surface electromyographic (EMG) signal data from a pair of muscles in the subject at a specific frequency, wherein the EMG signal data comprises one EMG signal per each muscle at the specific frequency;
   ii) processing the EMG signal data to determine an intermuscular coherence (IMC) phase of response between the pair of muscles at the specific frequency;
   iii) repeating steps i) and ii) across a frequency range; and
   iv) analyzing variability of the IMC phase of response between the pair of muscles across the frequency range to determine a phase variance value,
   wherein the phase variance value is calculated as the standard deviation of an average phase difference between EMG signals per frequency across the frequency range, and
   wherein the phase variance value indicates that the subject suffers from the neurodegenerative disorder.

2. The method of claim 1, wherein the frequency range is about 5 Hz to about 80 Hz.

3. The method of claim 1, wherein the phase variance value and an IMC value indicate that the subject suffers from the neurodegenerative disorder.

4. The method of claim 3 further comprising causing a display interface to display the phase variance value plotted against the IMC value.

5. The method of claim 4, wherein the phase variance value of between about 0.2 to about 1.2 and the IMC value of equal to or less than about 0.023 indicates that the subject suffers from the neurodegenerative disorder.

6. The method of claim 4, wherein the phase variance value of between about 0 to about 0.6 and the IMC value of greater than about 0.023 indicates that the subject does not suffer from the neurodegenerative disorder.

7. The method of claim 5, wherein the phase variance value directly correlates to a severity of disease progression.

8. The method of claim 1, wherein the neurodegenerative disorder is amyotrophic lateral sclerosis (ALS), spinocerebellar ataxia, fronto-temporal dementia, or primary lateral sclerosis.

9. The method of claim 1, wherein the pair of muscles includes arm muscles, hand muscles, leg muscles, or respiratory muscles.

10. The method of claim 9, wherein the pair of arm muscles is a brachioradialis muscle and a bicep muscle.

11. The method of claim 1 further comprising causing a display interface to display a plot of the IMC phase of the response between the pair of muscles across the frequency range.

12. The method of claim 1 further comprising causing a display interface to display the phase variance value and an indication when the phase variance value exceeds a predetermined threshold value.

* * * * *